(12) United States Patent
Shvartsburg et al.

(10) Patent No.: US 8,841,608 B2
(45) Date of Patent: Sep. 23, 2014

(54) METHOD FOR ENHANCING THE RESOLVING POWER OF ION MOBILITY SEPARATIONS OVER A LIMITED MOBILITY RANGE

(71) Applicants: Alexandre A. Shvartsburg, Richland, WA (US); Keqi Tang, Richland, WA (US); Richard D. Smith, Richland, WA (US)

(72) Inventors: Alexandre A. Shvartsburg, Richland, WA (US); Keqi Tang, Richland, WA (US); Richard D. Smith, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 13/861,511

(22) Filed: Apr. 12, 2013

(65) Prior Publication Data

US 2013/0299690 A1 Nov. 14, 2013

Related U.S. Application Data

(60) Provisional application No. 61/646,748, filed on May 14, 2012.

(51) Int. Cl.
*G01N 27/62* (2006.01)
*H01J 49/00* (2006.01)

(52) U.S. Cl.
CPC .......... *H01J 49/0031* (2013.01); *G01N 27/622* (2013.01)
USPC ............................ 250/282; 250/290; 250/287

(58) Field of Classification Search
USPC ................................................ 250/281–300
See application file for complete search history.

(56) References Cited

U.S. PATENT DOCUMENTS

| | | | |
|---|---|---|---|
| 6,914,241 B2 * | 7/2005 | Giles et al. | 250/286 |
| 7,449,683 B2 * | 11/2008 | Shvartsburg et al. | 250/287 |
| 2006/0219889 A1 | 10/2006 | Shvartsburg et al. | |
| 2010/0207022 A1 | 8/2010 | Tang et al. | |

OTHER PUBLICATIONS

Tolmachev et al., 'Charge Capacity Limitations of Radio Frequency Ion Guides in Their Use for Improved Ion Accumulation and Trapping in Mass Spectrometry', 2000, Anal. Chem. vol. 72, pp. 970-978.*
Shvartsburg, A. A., et al., Fundamentals of Traveling Wave Ion Mobility Spectrometry, Analytical Chemistry, 80, 24, 2008, 9689-9699.

* cited by examiner

*Primary Examiner* — Jack Berman
*Assistant Examiner* — Eliza Osenbaugh-Stewart
(74) *Attorney, Agent, or Firm* — A. J. Gokcek

(57) ABSTRACT

A method for raising the resolving power, specificity, and peak capacity of conventional ion mobility spectrometry is disclosed. Ions are separated in a dynamic electric field comprising an oscillatory field wave and opposing static field, or at least two counter propagating waves with different parameters (amplitude, profile, frequency, or speed). As the functional dependencies of mean drift velocity on the ion mobility in a wave and static field or in unequal waves differ, only single species is equilibrated while others drift in either direction and are mobility-separated. An ion mobility spectrum over a limited range is then acquired by measuring ion drift times through a fixed distance inside the gas-filled enclosure. The resolving power in the vicinity of equilibrium mobility substantially exceeds that for known traveling-wave or drift-tube IMS separations, with spectra over wider ranges obtainable by stitching multiple segments. The approach also enables low-cutoff, high-cutoff, and bandpass ion mobility filters.

21 Claims, 4 Drawing Sheets

US 8,841,608 B2

METHOD FOR ENHANCING THE RESOLVING POWER OF ION MOBILITY SEPARATIONS OVER A LIMITED MOBILITY RANGE

CROSS-REFERENCE TO RELATED APPLICATIONS

This application claims priority to U.S. Provisional Application Ser. No. 61/646,748, filed May 14, 2012, titled "METHOD FOR ENHANCING THE RESOLVING POWER OF ION MOBILITY SEPARATIONS OVER A LIMITED MOBILITY RANGE," hereby incorporated by reference in its entirety for all of its teachings.

STATEMENT REGARDING FEDERALLY SPONSORED RESEARCH OR DEVELOPMENT

The invention was made with Government support under Contract DE-AC05-76RLO1830, awarded by the U.S. Department of Energy. The Government has certain rights in the invention.

TECHNICAL FIELD

This invention relates to analytical separations and, more specifically, ion mobility spectrometry (IMS).

BACKGROUND OF THE INVENTION

IMS involves separation, characterization, or identification of ions based on their transport through gases driven by electric field. In conventional IMS considered here, separation is based on the absolute mobility (K) at moderate field intensity.

As for any separation method, a major IMS performance metric is the resolving power (R) that determines the achievable feature resolution and peak capacity. The value of R in drift-tube (DT) IMS scales as the square root of drift voltage and has been raised by increasing that voltage, currently up to R~170 (for singly-charged ions) at 14 kV. Further resolution gains along this path are impeded by the difficulty and cost of generating, isolating, and safely using voltages much above 10 kV. Conventional IMS was also implemented in "differential mobility analyzers" (DMA), where ions are filtered while pulled by a fixed electric field across a perpendicular high-speed gas flow in a narrow channel. The DMA resolving power also increases at higher voltages across the channel, and has been similarly limited to ~80 (achieved at 10 kV).

One alternative to voltage increases is extending the ion residence in DTIMS using gas counter-flow (Loboda et al., *J. Am. Soc. Mass Spectrom.* 2006, 17, 691). While R~40 attained in that system exceeds the "diffusion limit" defined by drift voltage for a stationary gas by fourfold, it is still much below the best DTIMS benchmarks, and achieving much greater R values is complicated by inevitable flow non-uniformity across the tube.

Another alternative is replacing a fixed electric field by time-dependent fields. The "cyclotron IMS" (Merenbloom et al., *Anal. Chem.* 2009, 81, 1482), where a potential gradient is switched (using individually addressed electrodes) to chase ions around a circular track, has reached an exceptional R~400-600. However, that approach is complex to implement and has poor sensitivity because of large ion losses in successive turns around the loop.

In a different approach of traveling-wave (TW) IMS adopted in the IMS/time-of-flight MS instruments of the Synapt family, ions are separated while "surfing" an oscillatory field wave propagated along a tunnel using individually addressed electrodes. Here the losses are minimal thanks to RF confinement, but the resolving power has been low at approximately 10-40. Such performance has precluded many IMS applications, and improving the resolution in TWIMS to (at least) the level of frontline DTIMS systems is topical.

Another desired capability is effective selection of ions with K values within a certain range, to prevent the saturation of charge capacity of devices storing ions for pulsed injection into subsequent IMS/MS or MS stages. For example, the ion accumulation funnel at an ESI/IMS interface commonly fills up in <10% of the IMS separation time. This causes major ion losses and compresses the dynamic range, unless elaborate multiplexing schemes are implemented. Similarly, the dynamic range of ion trap MS platforms is limited by the ion trap charge capacity.

What is needed are ion mobility devices and methods that separate or filter ions with higher resolving power.

SUMMARY OF THE INVENTION

Ions are separated in a gas-filled enclosure by oscillatory electric field wave and counter field that pull ions in opposite directions. That counter field can be a static field or another oscillatory field wave with parameters (amplitude, profile, frequency, speed, and combinations thereof) differing from that of the first wave and propagating in the opposite direction.

In one embodiment, ions with mobility above a certain threshold move with the first oscillatory field wave, while others move against it. Ions moving with that wave—from a source to a detector or following stage—are transmitted and registered, whereas ions moving against it are swiped back from the detector and removed. Alternatively, ions moving against the first wave are transmitted and registered, whereas ions moving with it are eliminated. Thus the device operates as a high- or low-mobility filter. In an alternative embodiment, ions within a particular mobility range are selected by consecutive low- and high-mobility filters.

In one embodiment, a method of increasing the resolving power of ion mobility separations is disclosed. Times of ion drift through a fixed distance inside the enclosure are measured, and an ion mobility spectrum over a limited mobility range is thus acquired.

In one embodiment, parameters of the first and second electric fields are adjusted to improve separation over the mobility range of desired width and position.

In one embodiment, at least one of the electric field waves has the harmonic or sinusoidal profile. In another embodiment, at least one of those waves is a superposition of multiple harmonic waveforms.

In one embodiment, the mobility range for a "zoom" at higher resolving power is selected in a data-dependent fashion, based on information about features in an ion mobility spectrum measured at a lower resolving power. The information includes, but is not limited to, peak width, shape, position, intensity, and combinations thereof. Several successive "zoom" steps of increasing resolving power over progressively narrower mobility ranges comprising the features of interest are possible.

Separation metrics can be improved over a mobility range by concatenating spectra acquired with increased resolving power over multiple narrower mobility segments within that range using different parameters of the first electric field or the opposing second electric field.

Filtered ions can be transmitted for downstream mass spectrometry (MS), IMS, or IMS/MS analyses. The disclosed methods are capable of rejecting unwanted ions (chemical noise) inevitably produced by known ionization sources. In an application, this helps one to avoid exceeding the charge capacity of electrodynamic funnel or other traps that accumulate ions prior to MS or IMS/MS measurements.

DETAILED DESCRIPTION OF THE PREFERRED EMBODIMENTS

Figure 1:
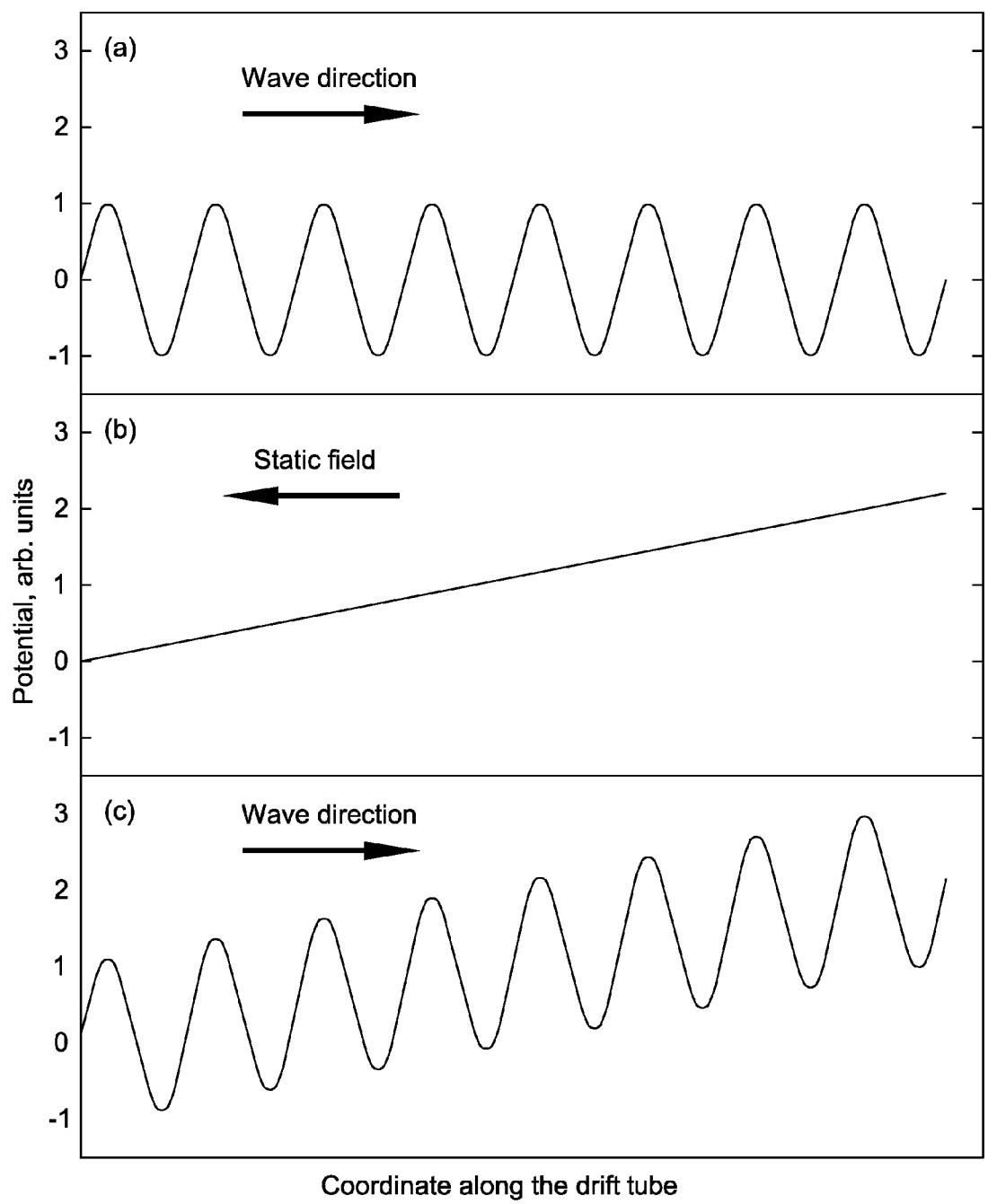
FIG. 1 illustrates: (a) an electric field wave such as utilized in TWIMS, propagating from the ion source toward the detector; (b) a static electric field such as used in DTIMS, pointed opposite to the wave direction of (a); (c) superposition of the field wave in (a) and field in (b), according to one embodiment of the invention.

The resolving power and thus resolution and peak capacity of IMS using the TWIMS paradigm can be significantly raised over a limited mobility range by applying a "retarding" electric field opposite to the direction of oscillatory field wave. This regime enables a "zoom" mode with theoretically unlimited resolving power gain, at the cost of narrower mobility range and extended separation time. The retarding field can be static or an oscillatory wave propagated contrary to the first wave direction with different parameters—the amplitude, waveform profile, frequency, or speed.

The time-averaged drift velocity of an ion in a field wave depends on its mobility K non-linearly: approximately as $K^2$ over a broad mobility range (Shvartsburg and Smith, *Anal. Chem.* 2008, 80, 9689). Conversely, the drift velocity in static field is linear with K (rigorously in the low-field limit, but in practice also at moderate fields typical for existing TWIMS implementations). Hence, the combination of a wave propagated in one direction and opposing static field would equilibrate ions of single mobility $K_{eq}$, while those of higher and lower K move with and against the wave, respectively. With the wave pointed from an ion source to a detector, species with $K > K_{eq}$ would be transmitted and registered and those with $K < K_{eq}$ would be swiped back and removed. Further, species with K moderately above $K_{eq}$ would transit slowly and spend long time in a separator, substantially elevating the resolving power in that range. The R values decrease with increasing K, from a theoretically infinite at K just above $K_{eq}$ to the baseline TWIMS limit at $K \gg K_{eq}$. Ions with mobility exceeding a certain threshold $K_{Th}$ are pushed by a wave at its speed and not separated, hence optimally one should arrange $K_{eq} \ll K_{Th}$. If the wave points to the ion source, species with $K < K_{eq}$ would conversely be transmitted, with the resolving power substantially elevated for K moderately below $K_{eq}$. Then R values decrease with decreasing K, from a theoretically infinite at K just below $K_{eq}$ to the baseline TWIMS limit at $K \ll K_{eq}$.

The time-averaged velocity of ions in a field wave of any profile scales with respect to K not strictly as $K^2$, but in a complex nonlinear manner that depends on that profile and wave speed, and varies over different K ranges (Shvartsburg and Smith, *Anal. Chem.* 2008, 80, 9689). In particular, the dependence can be stronger or weaker than $K^2$, even stronger over some K ranges and weaker over others for a given waveform. Hence two counter propagating waves with different parameters (amplitude, profile, frequency, or speed) would also equilibrate ions of single mobility only, with other species drifting in either direction. This regime would also substantially elevate the resolving power, in principle to infinity—while slowing the separation—in a limited mobility range above or below $K_{eq}$. While this modality was exemplified for two waves with differing parameters, three or more superposed waveforms may be utilized for optimum operation or hardware considerations. In terms of the dependence of drift velocity on K, a counter propagating wave may be engineered to come closer to the primary wave than a static field that provides the linear K dependence. Hence superposition of two or more waves may augment the IMS resolution more uniformly and over a wider mobility range than a wave combined with opposing static field as described above.

A high-resolution IMS spectrum over a broader mobility range may be obtained by stitching adjacent or partly overlapping segments individually acquired over limited ranges above or below $K_{eq}$, by stepping over a series of appropriately selected $K_{eq}$ values. In principle, one can continue raising the resolution indefinitely while decreasing the covered mobility range and separation speed. This is parallel to the "zoom" mode in common MS platforms.

Figure 4:
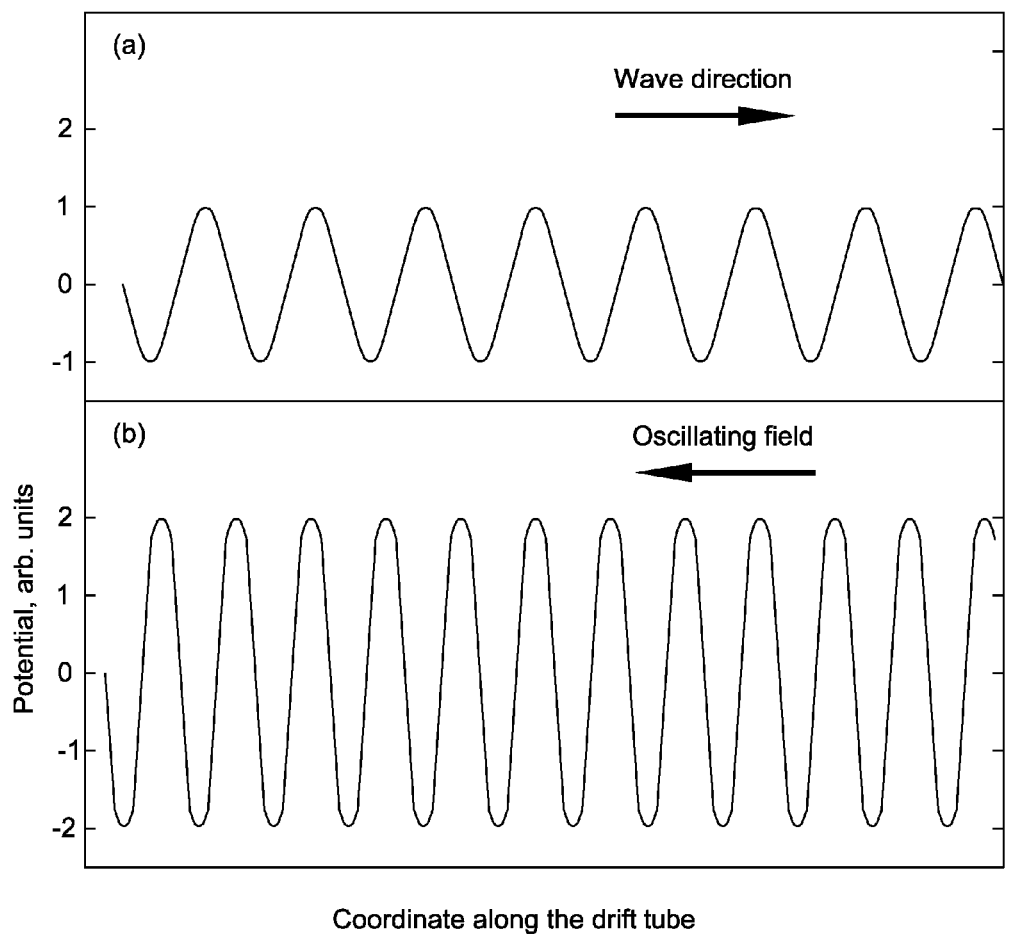
FIG. 4 illustrates: (a) an electric field wave such as utilized in TWIMS, propagating from the ion source toward the detector; (b) an oscillatory field wave with parameters differing from those of the electric field wave of (a) and propagated in the direction opposite to the wave direction of (a).

FIG. 1 schematically illustrates (a) an oscillatory electric field wave such as utilized in TWIMS, propagating from the ion source toward the detector; (b) a static electric field such as used in DTIMS, pointed opposite to the wave direction of (a); (c) superposition of the field wave in (a) and the opposing field in (b), according to one embodiment of the present invention. FIG. 4 schematically illustrates (a) an electric field wave such as utilized in TWIMS, propagating from the ion source toward the detector; (b) an oscillatory field wave with parameters differing from those of the electric field wave of (a) and propagated in the direction opposite to the wave direction of (a). In this example, as illustrated in FIG. 4, the two waves (a) and (b) have different amplitudes and frequencies.

Figure 2:
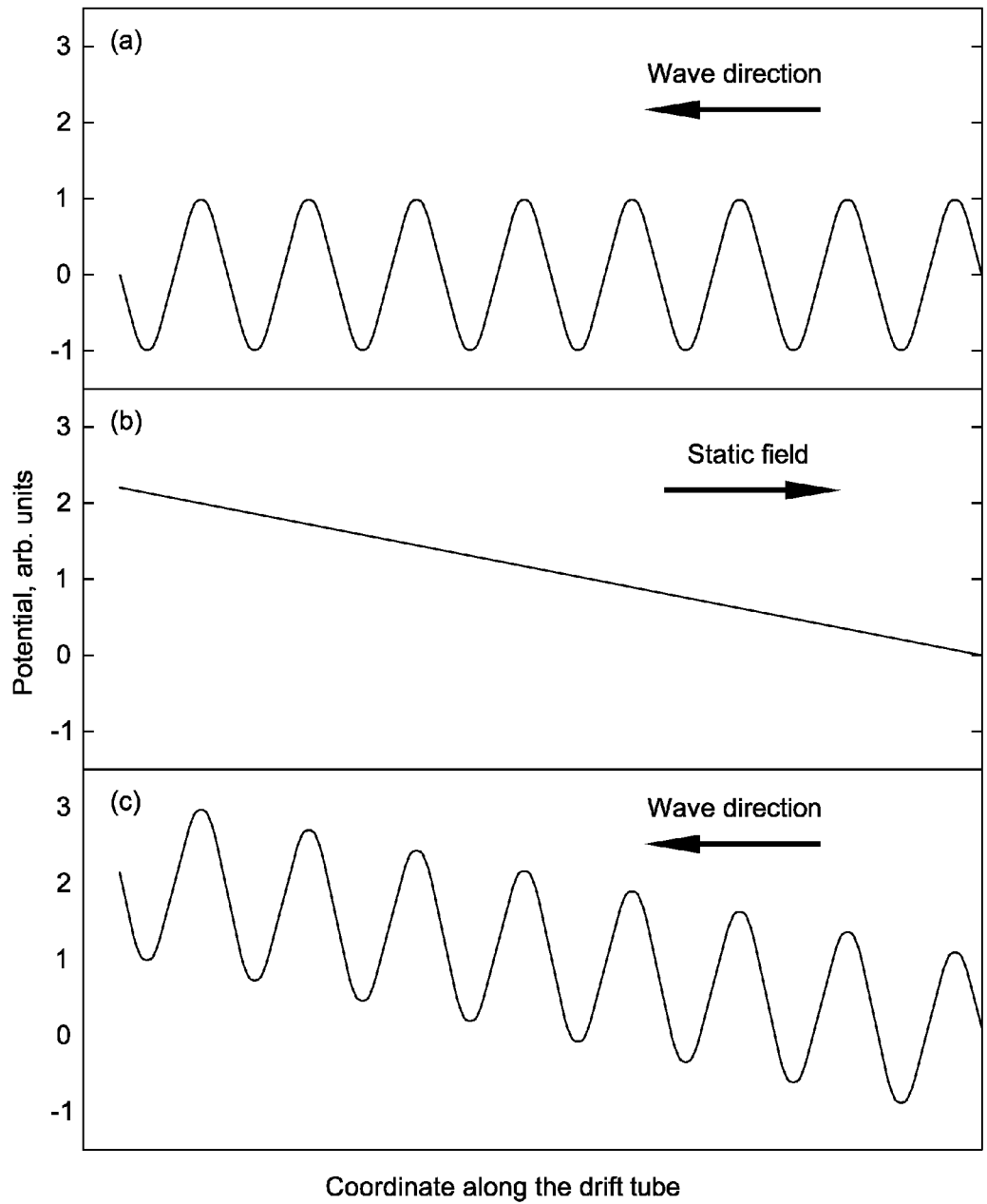
FIG. 2 illustrates: (a) an electric field wave such as utilized in TWIMS, propagating "backward" toward the ion source; (b) a static electric field such as used in DTIMS, pointed opposite to the wave direction of (a); (c) superposition of the field wave in (a) and field in (b), according to another embodiment of the invention.

FIG. 2 schematically illustrates: (a) an oscillatory electric field wave utilized in TWIMS, propagating "backward" toward the ion source; (b) a static electric field used in DTIMS, pointed opposite to the wave direction of (a); (c) superposition of the field wave in (a) and the opposing field in (b), according to another embodiment of the invention.

Figure 3:
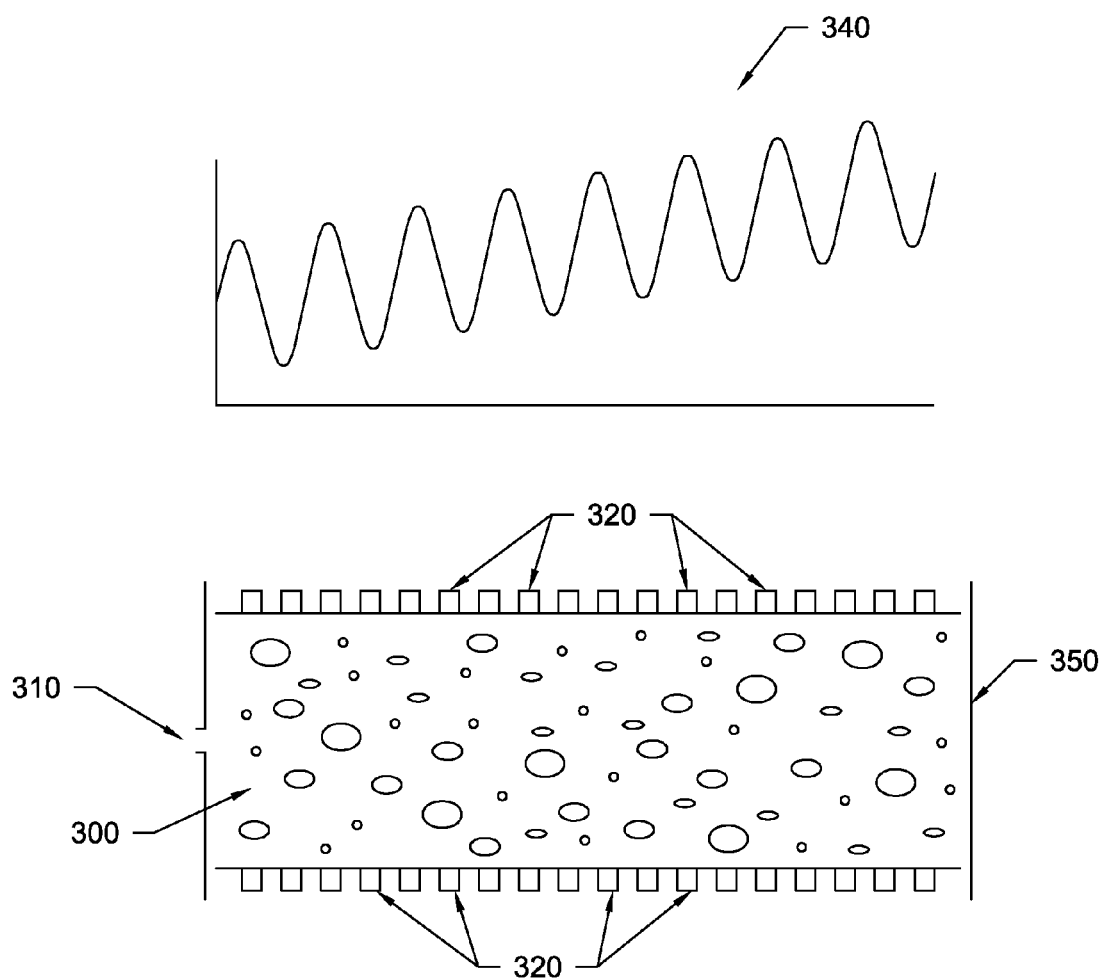
FIG. 3 illustrates an IMS system with superposition of the electric fields along the length thereof, according to one embodiment of the invention.

FIG. 3 illustrates an IMS system with superposition of the electric fields along the length thereof, according to one embodiment of the invention. The system includes a drift cell 300, ion injection inlet 310, electrodes 320, and detector 350. The superposition of the electric fields 340 travels along the length of the drift cell 300.

In one embodiment, ions are injected into the drift cell 300 through the inlet 310. The drift cell 300 contains an inert buffer gas and features the electric field 340, generated by dynamically applying proper voltages to the electrodes 320. The detector 350 detects ions exiting the drift cell 300 outlet and produces electrical signals indicative thereof.

The present invention would permit raising the resolving power in successive zoom modes, while maintaining broad spectral coverage in the regular TWIMS regime. The approach could be applied data-dependently, where full spectra are acquired in the regular TWIMS mode and peaks are inspected for proper (near-Gaussian) shape and width matching the calculations or measurements for model species of known single structure. Such selection could be performed manually or automatically, with software progressively zooming on segments where the peak asymmetry, undue kurtosis, and/or broadening indicate unresolved species until the shape and/or width criteria are satisfied or zoom level is maximized. This mode is extendable to IMS coupled to various MS platforms, including ToFMS, FTMS, and quadrupole MS, and FAIMS/IMS systems.

The wave and field combinations described above may remove species with mobilities either below or above a certain threshold by pushing them away from the ion detector. In particular, a low-K and a high-K cutoff stage—with unequal cutoff values—may be arranged in sequence to create a bandpass filter that transmits ions within a limited mobility range. Either stage may be positioned first, and the center and width of the pass band would be rapidly adjustable by varying the parameters of either or both stages. The band can be scanned across the mobility range to sequentially examine multiple or all segments in the MS or other downstream stage(s).

In another embodiment, species with $K>K_{eq}$ and $K<K_{eq}$ that travel in opposite directions are processed separately by detectors or downstream analytical stages situated at the opposite ends of the separation enclosure. Such stages may include mass spectrometers, other ion mobility spectrometers, spectroscopes, and combinations thereof.

Low-mobility, high-mobility, and bandpass filters described above could simplify the ion mixtures submitted to downstream MS, IMS/MS, spectroscopic, or other analyses, reject chemical noise from ionization sources, and help reducing and preventing the saturation of charge capacity of electrodynamic funnel traps or other traps that accumulate and store ions prior to MS, IMS/MS, spectroscopic, or other measurements.

Another application is with stand-alone IMS analyzers, where higher resolution and specificity are much desired but were deemed precluded by the weight, size, and power constraints stringently limiting the drift voltage. The methods of the present invention work at any gas pressure, and a retarding field or wave can be added to the primary wave using existing electrical architecture with no significant increase of power consumption. These factors make the invention attractive for portable devices, especially considering that the detection of explosives, chemical warfare agents, or atmospheric or industrial pollutants normally involves targeted analyses that would especially benefit from the zoom mode.

The advantages of the present invention are described above in terms of the resolving power, although the analytical performance in specific applications is commonly expressed via the metrics of resolution, specificity, or peak capacity. For a given analyte, those quantities scale linearly with the instrumental resolving power and hence would improve in proportion.

The present invention has been described in terms of specific embodiments incorporating details to facilitate the understanding of the principles of construction and operation of the invention. As such, references herein to specific embodiments and details thereof are not intended to limit the scope of the claims appended hereto. It will be apparent to those skilled in the art that modifications can be made in the embodiments chosen for illustration without departing from the spirit and scope of the invention.

We claim:

1. A method of increasing resolving power, feature resolution, specificity, or peak capacity of ion mobility separations comprising:
   a. propagating a first oscillatory electric field wave in a first direction, which pushes ions through a gas-filled enclosure in the first direction;
   b. applying a second electric field in a direction opposite to the first direction, which pushes ions in the opposite direction; and
   c. measuring times of ion drift through a fixed distance inside the enclosure to acquire an ion mobility spectrum over a limited mobility range;
   wherein the second electric field is an oscillatory field wave with parameters differing from those of the first field wave and propagated in the direction opposite to the first direction, wherein the parameters are at least one of the following: amplitude, profile, frequency, speed, and combinations thereof.

2. The method of claim 1 wherein the parameters of the first field wave and the second field are adjusted to improve separation over the mobility range of desired width and position.

3. The method of claim 2 wherein the mobility range is selected in a data-dependent fashion, based on information about features in an ion mobility spectrum previously measured at a lower resolving power.

4. The method of claim 3 wherein the information includes at least one of the following: peak width, shape, position, intensity, and combinations thereof.

5. The method of claim 2 wherein separation metrics are improved over the mobility range by concatenating spectra acquired with increased resolving power over multiple narrower mobility segments using different parameters of the first field wave or the opposing second field.

6. The method of claim 5 wherein the multiple narrower mobility segments are adjacent to cover the mobility range.

7. The method of claim 1 wherein at least one of the first and second field waves has a harmonic profile.

8. The method of claim 1 wherein at least one of the first and second field is a superposition of multiple harmonic waveforms.

9. The method of claim 1 wherein ions with mobility above a certain cutoff drift in the direction of the first field wave while ions with lower mobility drift in the opposite direction.

10. The method of claim 9 wherein drift times for ions traveling in both directions are measured.

11. The method of claim 1 wherein ions with mobility above a certain cutoff drift in the direction of the second field while ions with lower mobility drift in the opposite direction.

12. The method of claim 11 wherein drift times for ions traveling in both directions are measured.

13. The method of claim 1 wherein separated ions are further analyzed by at least one of the following: conventional ion mobility spectrometry, differential ion mobility spectrometry, mass spectrometry, spectroscopy, and combinations thereof.

14. A method of filtering ions with mobilities above or below a pre-determined cutoff comprising:
   a. propagating a first oscillatory electric field wave in a first direction, which pushes ions through a gas-filled enclosure in the first direction;
   b. applying a second electric field in a direction opposite the first direction, which pushes ions in the opposite direction; and c. allowing ions traveling in either the first direction or the opposite direction to be transmitted while removing ions traveling in the other of the directions;

wherein the second electric field is an oscillatory field wave with parameters differing from those of the first field wave and propagated in the direction opposite to the first direction, wherein the parameters are at least one of the following: amplitude, profile, frequency, speed, and combinations thereof.

15. The method of claim 14 further comprising producing a low-mobility cutoff followed by a high-mobility cutoff, wherein the low-mobility cutoff is lower than the high-mobility cutoff such that ions transmitted fall within a limited mobility range.

16. The method of claim 14 further comprising producing a high-mobility cutoff followed by a low-mobility cutoff, wherein the high-mobility cutoff is higher than the low-mobility cutoff such that ions transmitted fall within a limited mobility range.

17. The method of claim 14 wherein at least one of the first and second field has a harmonic profile.

18. The method of claim 14 wherein at least one of the first and the second field is a superposition of multiple harmonic waveforms.

19. The method of claim 14 wherein separated ions are further analyzed by at least one of the following: conventional ion mobility spectrometry, differential ion mobility spectrometry, mass spectrometry, spectroscopy, and combinations thereof.

20. The method of claim 14 further comprising placing an ion source upstream of the gas-filled enclosure, wherein the method operates to reject chemical noise from the source.

21. The method of claim 14 wherein the ions have K values within a predetermined range to prevent saturation of charge capacity of downstream devices storing the ions, wherein the devices are at least one of the following: Paul and Penning traps, electrodynamic ion funnel traps, quadrupole or rectilinear ion traps, C-traps, Orbitraps, and cells of ion cyclotron resonance instruments.

* * * * *